(12) United States Patent
Braig et al.

(10) Patent No.: US 8,951,495 B2
(45) Date of Patent: Feb. 10, 2015

(54) ODOR-INHIBITING COMPOSITIONS

(75) Inventors: Volker Braig, Weinheim-Lützelsachsen (DE); Thomas Daniel, Waldsee (DE); Rupert Konradi, Ladenburg (DE); Herbert Platsch, Mannheim (DE); Bettina Sobotka, Mannheim (DE); Axel Jentzsch, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 204 days.

(21) Appl. No.: 12/861,299

(22) Filed: Aug. 23, 2010

(65) Prior Publication Data

US 2011/0053767 A1 Mar. 3, 2011

Related U.S. Application Data

(60) Provisional application No. 61/236,896, filed on Aug. 26, 2009.

(51) Int. Cl.
```
C01B 15/04      (2006.01)
C01B 15/043     (2006.01)
C01B 15/047     (2006.01)
C01G 9/00       (2006.01)
C08F 20/06      (2006.01)
A61L 15/18      (2006.01)
A61F 13/84      (2006.01)
A61L 15/46      (2006.01)
```

(52) U.S. Cl.
CPC ............ *A61L 15/18* (2013.01); *A61F 13/8405* (2013.01); *A61L 15/46* (2013.01); *A61L 2300/102* (2013.01); *A61L 2300/11* (2013.01)
USPC ........... 423/582; 423/583; 423/622; 423/635; 526/317.1; 526/328

(58) Field of Classification Search
USPC ............ 423/581, 582, 592.1, 622; 526/317.1, 526/328
See application file for complete search history.

(56) References Cited

U.S. PATENT DOCUMENTS

| | | | |
|---|---|---|---|
| 1,953,526 A * | 4/1934 | Ainslie et al. ................. | 604/359 |
| 4,363,322 A | 12/1982 | Andersson | |
| 4,541,871 A | 9/1985 | Obayashi et al. | |
| 4,666,983 A | 5/1987 | Tsubakimoto et al. | |
| 4,734,478 A | 3/1988 | Tsubakimoto et al. | |
| 4,905,917 A * | 3/1990 | Fetzer et al. ................. | 241/30 |
| 5,004,761 A | 4/1991 | Yada et al. | |
| 5,281,683 A | 1/1994 | Yano et al. | |
| 5,331,059 A | 7/1994 | Engelhardt et al. | |
| 5,409,771 A | 4/1995 | Dahmen et al. | |
| 5,532,323 A | 7/1996 | Yano et al. | |
| 5,574,121 A | 11/1996 | Irie et al. | |
| 6,143,821 A | 11/2000 | Houben | |
| 6,239,230 B1 | 5/2001 | Eckert et al. | |
| 6,241,928 B1 | 6/2001 | Hatsuda et al. | |
| 6,265,488 B1 | 7/2001 | Fujino et al. | |
| 6,472,478 B1 | 10/2002 | Funk et al. | |
| 6,710,141 B1 | 3/2004 | Heide et al. | |
| 6,809,158 B2 | 10/2004 | Ikeuchi et al. | |
| 6,939,991 B2 | 9/2005 | Thiel et al. | |
| 7,183,360 B2 | 2/2007 | Daniel et al. | |
| 7,199,211 B2 | 4/2007 | Popp et al. | |
| 7,250,481 B2 | 7/2007 | Jaworek et al. | |
| 7,557,245 B2 | 7/2009 | Nordhoff et al. | |
| 7,652,111 B2 | 1/2010 | Hermeling et al. | |
| 7,687,596 B2 | 3/2010 | Hermeling et al. | |
| 7,754,822 B2 | 7/2010 | Daniel et al. | |
| 7,772,420 B2 | 8/2010 | Hermeling et al. | |
| 7,803,969 B2 | 9/2010 | Nordhoff et al. | |
| 2003/0098115 A1 * | 5/2003 | Dodge et al. .................. | 156/167 |
| 2005/0165208 A1 | 7/2005 | Popp et al. | |
| 2005/0209411 A1 | 9/2005 | Nestler et al. | |
| 2009/0012488 A1 | 1/2009 | Braig et al. | |
| 2010/0010176 A1 | 1/2010 | Losch et al. | |
| 2010/0029866 A1 | 2/2010 | Losch et al. | |

FOREIGN PATENT DOCUMENTS

| | | |
|---|---|---|
| DE | 3314019 A1 | 1/1984 |
| DE | 35 23 617 A1 | 1/1986 |
| DE | 3713601 A1 | 11/1988 |
| DE | 38 25 366 A1 | 2/1989 |
| DE | 40 20 780 C1 | 8/1991 |
| DE | 19543368 A1 | 5/1997 |
| DE | 19646484 A1 | 5/1997 |
| DE | 19807502 A1 | 9/1999 |
| DE | 102 04 937 A1 | 8/2003 |
| DE | 10204938 A1 | 8/2003 |
| DE | 10331450 A1 | 1/2005 |
| DE | 10331456 A1 | 2/2005 |
| DE | 10334584 A1 | 2/2005 |
| DE | 10355401 A1 | 6/2005 |
| EP | 083022 A2 | 7/1983 |
| EP | 0450922 A2 | 10/1991 |
| EP | 530438 A1 | 3/1993 |
| EP | 543303 B1 | 5/1993 |
| EP | 0547847 A1 | 6/1993 |
| EP | 559476 A1 | 9/1993 |

(Continued)

OTHER PUBLICATIONS

Pal et al., "Structural, optical, and adsorption properties of ZnO2/poly(acrylic acid) hybrid thin porous films prepared by ionic strength controlled layer-by-layer method." J. of Colloid and Interface Sci., 332 (2009) 173-182. Available online as of Jan. 21, 2009.*

Buchholz et al. (eds.), *Modern Superabsorbent Polymer Technology*, New York: Wiley-VCH (1998).

International Search Report in PCT/EP2010/061719 dated Apr. 6, 2011.

*Primary Examiner* — Stanley Silverman
*Assistant Examiner* — Daniel Berns
(74) *Attorney, Agent, or Firm* — Marshall, Gerstein & Borun LLP

(57) ABSTRACT

The present invention relates to odor-inhibiting compositions comprising water-absorbing polymer particles and metal peroxides, and to the production thereof.

4 Claims, No Drawings

(56) References Cited

FOREIGN PATENT DOCUMENTS

| | | | |
|---|---|---|---|
| EP | 0632068 A1 | 1/1995 |
| EP | 0937736 A2 | 8/1999 |
| EP | 1034800 A1 | 9/2000 |
| EP | 1199327 A2 | 4/2002 |
| GB | 627512 A | 8/1949 |
| GB | 2377890 A | 1/2003 |
| JP | 2001/115042 A | 4/2001 |
| JP | 2002/247786 A | 8/2002 |
| WO | WO-90/15830 A1 | 12/1990 |
| WO | WO-93/21237 A1 | 10/1993 |
| WO | WO-01/38402 A1 | 5/2001 |
| WO | WO-02/32962 A2 | 4/2002 |
| WO | WO-02/055469 A1 | 7/2002 |
| WO | WO-03/031482 A1 | 4/2003 |
| WO | WO-03/078378 A1 | 9/2003 |
| WO | WO-03/095510 A1 | 11/2003 |
| WO | WO-03/104299 A1 | 12/2003 |
| WO | WO-03/104300 A1 | 12/2003 |
| WO | WO-03/104301 A1 | 12/2003 |
| WO | WO-2004/035514 A1 | 4/2004 |
| WO | WO-2007/104641 A2 | 9/2007 |
| WO | WO-2008/040715 A2 | 4/2008 |
| WO | WO-2008/052971 A1 | 5/2008 |
| WO | WO-2009/101060 A1 | 8/2009 |
| WO | WO-2010/096595 A2 | 8/2010 |

\* cited by examiner

ODOR-INHIBITING COMPOSITIONS

CROSS-REFERENCE TO RELATED APPLICATIONS

This application claims the benefit of U.S. Provisional Patent Application No. 61/236,896, filed Aug. 26, 2009, incorporated herein by reference in its entirety.

The present invention relates to odor-inhibiting compositions comprising water-absorbing polymer particles and metal peroxides, and to the production thereof.

Water-absorbing polymer particles are used to produce diapers, tampons, sanitary napkins and other hygiene articles, but also as water-retaining agents in market gardening. The water-absorbing polymer particles are also referred to as superabsorbents.

The production of water-absorbing polymer particles is described in the monograph "Modern Superabsorbent Polymer Technology", F. L. Buchholz and A. T. Graham, Wiley-VCH, 1998, pages 71 to 103.

The properties of the water-absorbing polymer particles can be adjusted, for example, via the amount of crosslinker used. With increasing amount of crosslinker, the centrifuge retention capacity (CRC) falls and the absorption under a pressure of 21.0 g/cm$^2$ (AUL0.3psi) passes through a maximum.

To improve the application properties, for example permeability of the swollen gel bed (SFC) in the diaper and absorption under a pressure of 49.2 g/cm$^2$ (AUL0.7psi), water-absorbing polymer particles are generally surface postcrosslinked. This increases the degree of crosslinking of the particle surface, which allows the absorption under a pressure of 49.2 g/cm$^2$ (AUL0.7psi) and the centrifuge retention capacity (CRC) to be at least partly decoupled. This surface postcrosslinking can be performed in the aqueous gel phase. Preferably, however, dried, ground and sieved-off polymer particles (base polymer) are surface coated with a surface postcrosslinker, thermally surface postcrosslinked and dried. Crosslinkers suitable for this purpose are compounds which can form covalent bonds with at least two carboxylate groups of the water-absorbing polymer particles.

JP 2001/39802 teaches the use of sodium percarbonate and sodium perborate as antimicrobial additives for water-absorbing compositions.

GB 627,512 discloses the use of zinc peroxide for odor inhibition in hygiene articles.

GB 2 377 890 describes oxidizing agents as odor-inhibiting additives in water-absorbing compositions.

JP 2001/115042 discloses water-absorbing compositions comprising water-absorbing polymer particles, inorganic peroxides and ethylenediaminetetraacetic acid.

It was an object of the present invention to provide improved odor-inhibiting compositions, especially odor-inhibiting compositions with improved storage stability.

The object is achieved by odor-inhibiting compositions comprising water-absorbing polymer particles and at least one metal peroxide, metal hyperoxide or metal ozonide.

The metal peroxide is preferably the peroxide of a metal of main group 1, of main group 2 and/or of transition group 2 of the Periodic Table of the Elements, more preferably the peroxide of a metal of transition group 2 of the Periodic Table of the Elements, most preferably zinc peroxide.

Suitable metal peroxides are, for example, lithium peroxide, strontium peroxide, barium peroxide, sodium peroxide, magnesium peroxide, calcium peroxide, potassium hyperoxide and zinc peroxide.

The inventive composition comprises preferably 0.001 to 5% by weight, preferably from 0.01 to 3% by weight, more preferably from 0.1 to 1.5% by weight, most preferably from 0.2 to 0.8% by weight, of the metal peroxide, metal hyperoxide or metal ozonide.

The inventive composition comprises preferably less than 10% by weight, preferentially less than 8% by weight, more preferably less than 6% by weight, most preferably less than 5% by weight, of water.

The inventive composition comprises preferably at least 90% by weight, more preferably at least 95% by weight, preferably at least 97% by weight, most preferably at least 98% by weight, of water-absorbing polymer particles.

The present invention is based on the finding that metal peroxides, metal hyperoxides and metal ozonides, especially zinc peroxide, have a good odor-inhibiting action, and the compositions produced therewith have a high storage stability.

The inventive compositions comprise preferably less than 1 ppm, particularly preferably less than 10 ppm, most preferably less than 5 ppm, of heavy metal ions. Heavy metal ions, especially iron ions, lead to catalytic decomposition of the metal peroxides, metal hyperoxides and metal ozonides and hence lower the storage stability of the inventive compositions.

The production of the water-absorbing polymer particles will be explained in detail hereinafter.

The water-absorbing polymer particles are produced, for example, by polymerizing a monomer solution or suspension comprising a) at least one ethylenically unsaturated monomer which bears acid groups and may be at least partly neutralized,
b) at least one crosslinker,
c) at least one initiator,
d) optionally one or more ethylenically unsaturated monomers copolymerizable with the monomers mentioned under a) and
e) optionally one or more water-soluble polymers, and are typically water-insoluble.

The monomers a) are preferably water-soluble, i.e. the solubility in water at 23° C. is typically at least 1 g/100 g of water, preferably at least 5 g/100 g of water, more preferably at least 25 g/100 g of water, most preferably at least 35 g/100 g of water.

Suitable monomers a) are, for example, ethylenically unsaturated carboxylic acids, such as acrylic acid, methacrylic acid and itaconic acid. Particularly preferred monomers are acrylic acid and methacrylic acid. Very particular preference is given to acrylic acid.

Further suitable monomers a) are, for example, ethylenically unsaturated sulfonic acids, such as styrenesulfonic acid and 2-acrylamido-2-methylpropanesulfonic acid (AMPS).

Impurities can have a considerable influence on the polymerization. The raw materials used should therefore have a maximum purity. It is therefore often advantageous to specially purify the monomers a). Suitable purification processes are described, for example, in WO 2002/055469 A1, WO 2003/078378 A1 and WO 2004/035514 A1. A suitable monomer a) is, for example, acrylic acid purified according to WO 2004/035514 A1 comprising 99.8460% by weight of acrylic acid, 0.0950% by weight of acetic acid, 0.0332% by weight of water, 0.0203% by weight of propionic acid, 0.0001% by weight of furfurals, 0.0001% by weight of maleic anhydride, 0.0003% by weight of diacrylic acid and 0.0050% by weight of hydroquinone monomethyl ether.

The proportion of acrylic acid and/or salts thereof in the total amount of monomers a) is preferably at least 50 mol %, more preferably at least 90 mol %, most preferably at least 95 mol %.

The monomers a) typically comprise polymerization inhibitors, preferably hydroquinone monoethers, as storage stabilizers.

The monomer solution comprises preferably up to 250 ppm by weight, preferably at most 130 ppm by weight, more preferably at most 70 ppm by weight, preferably at least 10 ppm by weight, more preferably at least 30 ppm by weight, especially around 50 ppm by weight, of hydroquinone monoether, based in each case on the unneutralized monomer a). For example, the monomer solution can be prepared by using an ethylenically unsaturated monomer bearing acid groups with an appropriate content of hydroquinone monoether.

Preferred hydroquinone monoethers are hydroquinone monomethyl ether (MEHQ) and/or alpha-tocopherol (vitamin E).

Suitable crosslinkers b) are compounds having at least two groups suitable for crosslinking. Such groups are, for example, ethylenically unsaturated groups which can be polymerized free-radically into the polymer chain, and functional groups which can form covalent bonds with the acid groups of the monomer a). In addition, polyvalent metal salts which can form coordinate bonds with at least two acid groups of the monomer a) are also suitable as crosslinkers b).

Crosslinkers b) are preferably compounds having at least two polymerizable groups which can be polymerized free-radically into the polymer network. Suitable crosslinkers b) are, for example, ethylene glycol dimethacrylate, diethylene glycol diacrylate, polyethylene glycol diacrylate, allyl methacrylate, trimethylolpropane triacrylate, triallylamine, tetraallylammonium chloride, tetraallyloxyethane, as described in EP 0 530 438 A1, di- and triacrylates, as described in EP 0 547 847 A1, EP 0 559 476 A1, EP 0 632 068 A1, WO 93/21237 A1, WO 2003/104299 A1, WO 2003/104300 A1, WO 2003/104301 A1 and DE 103 31 450 A1, mixed acrylates which, as well as acrylate groups, comprise further ethylenically unsaturated groups, as described in DE 103 31 456 A1 and DE 103 55 401 A1, or crosslinker mixtures, as described, for example, in DE 195 43 368 A1, DE 196 46 484 A1, WO 90/15830 A1 and WO 2002/032962 A2.

Preferred crosslinkers b) are pentaerythrityl triallyl ether, tetraalloxyethane, methylenebismethacrylamide, 15-tuply ethoxylated trimethylolpropane triacrylate, polyethylene glycol diacrylate, trimethylolpropane triacrylate and triallylamine.

Very particularly preferred crosslinkers b) are the polyethoxylated and/or -propoxylated glycerols which have been esterified with acrylic acid or methacrylic acid to give di- or triacrylates, as described, for example, in WO 2003/104301 A1. Di- and/or triacrylates of 3- to 10-tuply ethoxylated glycerol are particularly advantageous. Very particular preference is given to di- or triacrylates of 1- to 5-tuply ethoxylated and/or propoxylated glycerol. Most preferred are the triacrylates of 3- to 5-tuply ethoxylated and/or propoxylated glycerol, especially the triacrylate of 3-tuply ethoxylated glycerol.

The amount of crosslinker b) is preferably 0.05 to 1.5% by weight, more preferably 0.1 to 1% by weight, most preferably 0.3 to 0.6% by weight, based in each case on monomer a). With rising crosslinker content, the centrifuge retention capacity (CRC) falls and the absorption under a pressure of 21.0 g/cm$^2$ passes through a maximum.

The initiators c) used may be all compounds which generate free radicals under the polymerization conditions, for example thermal initiators, redox initiators, photoinitiators. Suitable redox initiators are sodium peroxodisulfate/ascorbic acid, hydrogen peroxide/ascorbic acid, sodium peroxodisulfate/sodium bisulfite and hydrogen peroxide/sodium bisulfite. Preference is given to using mixtures of thermal initiators and redox initiators, such as sodium peroxodisulfate/hydrogen peroxide/ascorbic acid. The reducing component used is, however, preferably a mixture of the sodium salt of 2-hydroxy-2-sulfinatoacetic acid, the disodium salt of 2-hydroxy-2-sulfonatoacetic acid and sodium bisulfite. Such mixtures are obtainable as Brüggolite® FF6 and Brüggolite® FF7 (Brüggemann Chemicals; Heilbronn; Germany).

Ethylenically unsaturated monomers d) copolymerizable with the ethylenically unsaturated monomers a) bearing acid groups are, for example, acrylamide, methacrylamide, hydroxyethyl acrylate, hydroxyethyl methacrylate, dimethylaminoethyl methacrylate, dimethylaminoethyl acrylate, dimethylaminopropyl acrylate, diethylaminopropyl acrylate, dimethylaminoethyl methacrylate, diethylaminoethyl methacrylate.

The water-soluble polymers e) used may be polyvinyl alcohol, polyvinylpyrrolidone, starch, starch derivatives, modified cellulose, such as methylcellulose or hydroxyethylcellulose, gelatin, polyglycols or polyacrylic acids, preferably starch, starch derivatives and modified cellulose.

Typically, an aqueous monomer solution is used. The water content of the monomer solution is preferably from 40 to 75% by weight, more preferably from 45 to 70% by weight, most preferably from 50 to 65% by weight. It is also possible to use monomer suspensions, i.e. monomer solutions with excess monomer a), for example sodium acrylate. With rising water content, the energy requirement in the subsequent drying rises, and, with falling water content, the heat of polymerization can only be removed inadequately.

For optimal action, the preferred polymerization inhibitors require dissolved oxygen. The monomer solution can therefore be freed of dissolved oxygen before the polymerization by inertization, i.e. flowing an inert gas through, preferably nitrogen or carbon dioxide. The oxygen content of the monomer solution is preferably lowered before the polymerization to less than 1 ppm by weight, more preferably to less than 0.5 ppm by weight, most preferably to less than 0.1 ppm by weight.

Suitable reactors are, for example, kneading reactors or belt reactors. In the kneader, the polymer gel formed in the polymerization of an aqueous monomer solution or suspension is comminuted continuously by, for example, contrarotatory stirrer shafts, as described in WO 2001/038402 A1. Polymerization on a belt is described, for example, in DE 38 25 366 A1 and U.S. Pat. No. 6,241,928. Polymerization in a belt reactor forms a polymer gel, which has to be comminuted in a further process step, for example in an extruder or kneader.

However, it is also possible to dropletize an aqueous monomer solution and to polymerize the droplets obtained in a heated carrier gas stream. This allows the process steps of polymerization and drying to be combined, as described in WO 2008/040715 A2 and WO 2008/052971 A1.

The acid groups of the resulting polymer gels have typically been partially neutralized. Neutralization is preferably carried out at the monomer stage. This is typically done by mixing in the neutralizing agent as an aqueous solution or preferably also as a solid. The degree of neutralization is preferably from 25 to 85 mol %, for "acidic" polymer gels more preferably from 30 to 60 mol %, most preferably from 35 to 55 mol %, and for "neutral" polymer gels more preferably from 65 to 80 mol %, most preferably from 70 to 75 mol %, for which the customary neutralizing agents can be used, preferably alkali metal hydroxides, alkali metal oxides, alkali metal carbonates or alkali metal hydrogencarbonates and also mixtures thereof. Instead of alkali metal salts, it is also possible to use ammonium salts, such as the salt of triethanolamine. Particularly preferred alkali metals are sodium and potassium, but very particular preference is given to sodium hydroxide, sodium carbonate or sodium hydrogencarbonate and also mixtures thereof.

However, it is also possible to carry out neutralization after the polymerization, at the stage of the polymer gel formed in the polymerization. It is also possible to neutralize up to 40 mol %, preferably 10 to 30 mol % and more preferably 15 to 25 mol % of the acid groups before the polymerization by adding a portion of the neutralizing agent actually to the monomer solution and setting the desired final degree of neutralization only after the polymerization, at the polymer gel stage. When the polymer gel is neutralized at least partly after the polymerization, the polymer gel is preferably comminuted mechanically, for example by means of an extruder, in which case the neutralizing agent can be sprayed, sprinkled or poured on and then carefully mixed in. To this end, the gel mass obtained can be repeatedly extruded for homogenization.

The polymer gel is then preferably dried with a belt drier until the residual moisture content is preferably 0.5 to 15% by weight, more preferably 1 to 10% by weight, most preferably 2 to 8% by weight, the residual moisture content being determined by EDANA (European Disposables and Nonwovens Association) recommended test method No. WSP 230.2-05 "Moisture Content". In the case of too high a residual moisture content, the dried polymer gel has too low a glass transition temperature $T_g$ and can be processed further only with difficulty. In the case of too low a residual moisture content, the dried polymer gel is too brittle and, in the subsequent comminution steps, undesirably large amounts of polymer particles with an excessively low particle size (fines) are obtained. The solids content of the gel before the drying is preferably from 25 to 90% by weight, more preferably from 35 to 70% by weight, most preferably from 40 to 60% by weight. Optionally, it is, however, also possible to use a fluidized bed drier or a paddle drier for the drying operation.

Thereafter, the dried polymer gel is ground and classified, and the apparatus used for grinding may typically be single- or multistage roll mills, preferably two- or three-stage roll mills, pin mills, hammer mills or vibratory mills.

The mean particle size of the polymer particles removed as the product fraction is preferably at least 200 µm, more preferably from 250 to 600 µm, very particularly from 300 to 500 µm. The mean particle size of the product fraction may be determined by means of EDANA (European Disposables and Nonwovens Association) recommended test method No. WSP 220.2-05 "Particle Size Distribution", where the proportions by mass of the screen fractions are plotted in cumulative form and the mean particle size is determined graphically. The mean particle size here is the value of the mesh size which gives rise to a cumulative 50% by weight.

The proportion of particles with a particle size of at least 150 µm is preferably at least 90% by weight, more preferably at least 95% by weight, most preferably at least 98% by weight.

Polymer particles with too small a particle size lower the permeability (SFC). The proportion of excessively small polymer particles (fines) should therefore be small.

Excessively small polymer particles are therefore typically removed and recycled into the process. This is preferably done before, during or immediately after the polymerization, i.e. before the drying of the polymer gel. The excessively small polymer particles can be moistened with water and/or aqueous surfactant before or during the recycling.

It is also possible in later process steps to remove excessively small polymer particles, for example after the surface postcrosslinking or another coating step. In this case, the excessively small polymer particles recycled are surface postcrosslinked or coated in another way, for example with fumed silica.

When a kneading reactor is used for polymerization, the excessively small polymer particles are preferably added during the last third of the polymerization.

When the excessively small polymer particles are added at a very early stage, for example actually to the monomer solution, this lowers the centrifuge retention capacity (CRC) of the resulting water-absorbing polymer particles. However, this can be compensated, for example, by adjusting the amount of crosslinker b) used.

When the excessively small polymer particles are added at a very late stage, for example not until an apparatus connected downstream of the polymerization reactor, for example to an extruder, the excessively small polymer particles can be incorporated into the resulting polymer gel only with difficulty. Insufficiently incorporated, excessively small polymer particles are, however, detached again from the dried polymer gel during the grinding, are therefore removed again in the course of classification and increase the amount of excessively small polymer particles to be recycled.

The proportion of particles having a particle size of at most 850 µm is preferably at least 90% by weight, more preferably at least 95% by weight, most preferably at least 98% by weight.

The proportion of particles having a particle size of at most 600 µm is preferably at least 90% by weight, more preferably at least 95% by weight, most preferably at least 98% by weight.

Polymer particles with too great a particle size lower the swell rate. The proportion of excessively large polymer particles should therefore likewise be small.

Excessively large polymer particles are therefore typically removed and recycled into the grinding of the dried polymer gel.

To further improve the properties, the polymer particles can be surface postcrosslinked. Suitable surface postcrosslinkers are compounds which comprise groups which can form covalent bonds with at least two carboxylate groups of the polymer particles. Suitable compounds are, for example, polyfunctional amines, polyfunctional amidoamines, polyfunctional epoxides, as described in EP 0 083 022 A2, EP 0 543 303 A1 and EP 0 937 736 A2, di- or polyfunctional alcohols, as described in DE 33 14 019 A1, DE 35 23 617 A1 and EP 0 450 922 A2, or β-hydroxyalkylamides, as described in DE 102 04 938 A1 and U.S. Pat. No. 6,239,230.

Additionally described as suitable surface postcrosslinkers are cyclic carbonates in DE 40 20 780 C1, 2-oxazolidone and its derivatives, such as 2-hydroxyethyl-2-oxazolidone in DE 198 07 502 A1, bis- and poly-2-oxazolidinones in DE 198 07 992 C1, 2-oxotetrahydro-1,3-oxazine and its derivatives in DE 198 54 573 A1, N-acyl-2-oxazolidones in DE 198 54 574 A1, cyclic ureas in DE 102 04 937 A1, bicyclic amide acetals in DE 103 34 584 A1, oxetanes and cyclic ureas in EP 1 199 327 A2 and morpholine-2,3-dione and its derivatives in WO 2003/031482 A1.

Preferred surface postcrosslinkers are ethylene carbonate, ethylene glycol diglycidyl ether, reaction products of polyamides with epichlorohydrin, and mixtures of propylene glycol and 1,4-butanediol.

Very particularly preferred surface postcrosslinkers are 2-hydroxyethyloxazolidin-2-one, oxazolidin-2-one and 1,3-propanediol.

In addition, it is also possible to use surface postcrosslinkers which comprise additional polymerizable ethylenically unsaturated groups, as described in DE 37 13 601 A1.

The amount of surface postcrosslinkers is preferably 0.001 to 2% by weight, more preferably 0.02 to 1% by weight, most preferably 0.05 to 0.2% by weight, based in each case on the polymer particles.

In a preferred embodiment of the present invention, polyvalent cations are applied to the particle surface in addition to the surface postcrosslinkers before, during or after the surface postcrosslinking.

The polyvalent cations usable in the process according to the invention are, for example, divalent cations such as the cations of zinc, magnesium, calcium and strontium, trivalent cations such as the cations of aluminum, tetravalent cations such as the cations of titanium and zirconium. Possible counterions are, for example, chloride, bromide, sulfate, hydrogensulfate, carbonate, hydrogencarbonate, nitrate, phosphate, hydrogenphosphate, dihydrogenphosphate and carboxylate, such as acetate and lactate. Aluminum sulfate and aluminum lactate are preferred. Apart from metal salts, it is also possible to use polyamines as polyvalent cations.

The amount of polyvalent cation used is, for example, 0.001 to 1.5% by weight, preferably 0.005 to 1% by weight, more preferably 0.02 to 0.8% by weight, based in each case on the polymer particles.

The surface postcrosslinking is typically performed in such a way that a solution of the surface postcrosslinker is sprayed onto the dried polymer particles. After the spraying, the polymer particles coated with surface postcrosslinker are dried thermally, and the surface postcrosslinking reaction can take place either before or during the drying.

The spraying of a solution of the surface postcrosslinker is preferably performed in mixers with moving mixing tools, such as screw mixers, disk mixers and paddle mixers. Particular preference is given to horizontal mixers such as paddle mixers, very particular preference to vertical mixers. The distinction between horizontal mixers and vertical mixers is made by the position of the mixing shaft, i.e. horizontal mixers have a horizontally mounted mixing shaft and vertical mixers a vertically mounted mixing shaft. Suitable mixers are, for example, horizontal Pflugschar® plowshare mixers (Gebr. Lödige Maschinenbau GmbH; Paderborn; Germany), Vrieco-Nauta continuous mixers (Hosokawa Micron BV; Doetinchem; the Netherlands), Processall Mixmill mixers (Processall Incorporated; Cincinnati; US) and Schugi Flexomix® (Hosokawa Micron BV; Doetinchem; the Netherlands). However, it is also possible to spray on the surface postcrosslinker solution in a fluidized bed.

The surface postcrosslinkers are typically used in the form of an aqueous solution. The content of nonaqueous solvent and/or total amount of solvent can be used to adjust the penetration depth of the surface postcrosslinker into the polymer particles.

When exclusively water is used as the solvent, a surfactant is advantageously added. This improves the wetting performance and reduces the tendency to form lumps. However, preference is given to using solvent mixtures, for example isopropanol/water, 1,3-propanediol/water and propylene glycol/water, where the mixing ratio by mass is preferably from 20:80 to 40:60.

The thermal drying is preferably carried out in contact driers, more preferably paddle driers, most preferably disk driers. Suitable driers are, for example, Hosokawa Bepex® horizontal paddle driers (Hosokawa Micron GmbH; Leingarten; Germany), Hosokawa Bepex® disk driers (Hosokawa Micron GmbH; Leingarten; Germany) and Nara paddle driers (NARA Machinery Europe; Frechen; Germany). Moreover, it is also possible to use fluidized bed driers.

The drying can be effected in the mixer itself, by heating the jacket or blowing in warm air. Equally suitable is a downstream drier, for example a shelf drier, a rotary tube oven or a heatable screw. It is particularly advantageous to mix and dry in a fluidized bed drier.

Preferred drying temperatures are in the range of 100 to 250° C., preferably 120 to 220° C., more preferably 130 to 210° C., most preferably 150 to 200° C. The preferred residence time at this temperature in the reaction mixer or drier is preferably at least 10 minutes, more preferably at least 20 minutes, most preferably at least 30 minutes, and typically at most 60 minutes.

Subsequently, the surface postcrosslinked polymer particles can be classified again, excessively small and/or excessively large polymer particles being removed and recycled into the process.

To further improve the properties, the surface postcrosslinked polymer particles can be coated or remoisturized.

The remoisturizing is carried out preferably at 30 to 80° C., more preferably at 35 to 70° C. and most preferably at 40 to 60° C. At excessively low temperatures, the water-absorbing polymer particles tend to form lumps, and, at higher temperatures, water already evaporates noticeably. The amount of water used for remoisturizing is preferably from 1 to 10% by weight, more preferably from 2 to 8% by weight and most preferably from 3 to 5% by weight. The remoisturizing increases the mechanical stability of the polymer particles and reduces their tendency to static charging.

Suitable coatings for improving the swell rate and the permeability (SFC) are, for example, inorganic inert substances, such as water-insoluble metal salts, organic polymers, cationic polymers and di- or polyvalent metal cations. Suitable coatings for dust binding are, for example, polyols. Suitable coatings for counteracting the undesired caking tendency of the polymer particles are, for example, fumed silica, such as Aerosil® 200, and surfactants, such as Span® 20.

The water-absorbing polymer particles have a moisture content of preferably 1 to 15% by weight, more preferably 2 to 10% by weight, most preferably 3 to 5% by weight, the moisture content being determined by EDANA (European Disposables and Nonwovens Association) recommended test method No. WSP 230.2-05 "Moisture Content".

The water-absorbing polymer particles have a centrifuge retention capacity (CRC) of typically at least 15 g/g, preferably at least 20 g/g, preferentially at least 22 g/g, more preferably at least 24 g/g, most preferably at least 26 g/g. The centrifuge retention capacity (CRC) of the water-absorbing polymer particles is typically less than 60 g/g. The centrifuge retention capacity (CRC) is determined by EDANA (European Disposables and Nonwovens Association) recommended test method No. WSP 241.2-05 "Centrifuge Retention Capacity".

The water-absorbing polymer particles have an absorption under a pressure of 49.2 g/cm$^2$ of typically at least 15 g/g, preferably at least 20 g/g, preferentially at least 22 g/g, more preferably at least 24 g/g, most preferably at least 26 g/g. The absorption under a pressure of 49.2 g/cm$^2$ of the water-absorbing polymer particles is typically less than 35 g/g. The absorption under a pressure of 49.2 g/cm$^2$ is determined analogously to EDANA (European Disposables and Nonwovens Association) recommended test method No. WSP 242.2-05 "Absorption under Pressure", except that a pressure of 49.2 g/cm² is established instead of a pressure of 21.0 g/cm².

The present invention further provides processes for producing the inventive compositions by i) mixing at least one metal peroxide, metal hyperoxide or metal ozonide together with water-absorbing polymer particles and/or ii) grinding at least one metal peroxide, metal hyperoxide or metal ozonide together with water-absorbing polymer particles and/or iii) spraying at least one metal peroxide, metal hyperoxide or metal ozonide onto water-absorbing polymer particles and iv) optionally mixing the composition obtained in i), ii) and/or iii) together with water-absorbing polymer particles.

Variant i) is preferred.

The type of mixing is not subject to any restriction and can be effected as early as in the course of production of the water-absorbing polymer particles, for example in the course of cooling after the surface postcrosslinking or the subsequent classifying, or in a specific mixer. Suitable mixers have already been described above for the surface postcrosslinking of the water-absorbing polymer particles.

The type of grinding is likewise not subject to any restriction. Suitable apparatuses have already been described above for the comminution of the water-absorbing polymer particles.

The type of spraying is not subject to any restriction.

In the production of powder mixtures from water-absorbing polymer particles and at least one metal peroxide, metal hyperoxide or metal ozonide, antidusting agents are advantageously used. Suitable antidusting agents are polyglycerols, polyethylene glycols, polypropylene glycols, random or block copolymers of ethylene oxide and propylene oxide. Further antidusting agents suitable for this purpose are the polyethoxylates or polypropoxylates of polyhydroxyl compounds, such as glycerol, sorbitol, trimethylolpropane, trimethylolethane and pentaerythritol. Examples thereof are n-tuply ethoxylated trimethylolpropane or glycerol, where n is an integer from 1 to 100. Further examples are block copolymers such as trimethylolpropane or glycerol which have been n-tuply ethoxylated and then m-tuply propoxylated overall, where n is an integer from 1 to 40 and m is an integer from 1 to 40. The sequence of the blocks may also be reversed. The antidusting agents can also be diluted with water.

In the case of powder mixtures, the density of the components to be mixed is important. There is then no separation when the densities of water-absorbing polymer particles and metal peroxide, metal hyperoxide or metal ozonide are similar, or the particles of the metal peroxide, metal hyperoxide or metal ozonide are much smaller than those of the water-absorbing polymer particles.

The present invention further provides hygiene articles comprising at least one inventive composition, especially hygiene articles for feminine hygiene, hygiene articles for light and heavy incontinence, or small animal litter.

The hygiene articles typically comprise a water-impervious backside, a water-pervious topside and, in between, an absorbent core of the inventive water-absorbing polymer particles and fibers, preferably cellulose. The proportion of the inventive water-absorbing polymer particles in the absorbent core is preferably 20 to 100% by weight, preferentially 50 to 100% by weight.

The water-absorbing polymer particles are tested by means of the test methods described below.

Methods:

The measurements should, unless stated otherwise, be carried out at an ambient temperature of 23±2° C. and a relative air humidity of 50±10%. The water-absorbing polymer particles are mixed thoroughly before the measurement.

Centrifuge Retention Capacity

The centrifuge retention capacity (CRC) is determined by EDANA recommended test method No. WSP 241.2-05 "Centrifuge Retention Capacity".

Bacteria-Induced Ammonia Release

DSM1 medium (Deutsche Sammlung von Mikroorganismen und Zellkulturen GmbH) was prepared from 5.0 g/l of peptone from meat (Merck KGaA; Darmstadt; Germany; Art. No. 1.07214) and 3.0 g/l of meat extract (Merck KGaA, Darmstadt; Germany; Art. No. 1103979) and adjusted to pH=7.0. 50 ml of DSM1 medium were inoculated to OD=0.1 with Proteus mirabilis ATCC 14153, and incubated in a 250 ml baffled Erlenmeyer flask at 37° C. and 220 rpm for 15 hours. The cultures thus produced had a cell density of about $10^9$ CFU/ml (OD=2.0-2.5).

The synthetic urine was prepared from 25 g/l of urea (sterile-filtered), 9.0 g/l of sodium chloride,) g/l of peptone from meat and 1 g/l of meat extract. The synthetic urine was autoclaved before addition of a sterile-filtered concentrated urea solution.

125 ml polypropylene histology beakers were autoclaved, and the amount of water-absorbing polymer particles needed to absorb 50 ml of synthetic urine was introduced (calculated from the centrifuge retention capacity). Then 50 ml of synthetic urine were inoculated with 50 µl of bacterial strain solution corresponding to a total concentration of approx. $10^6$ CFU/ml and mixed with the water-absorbing polymer particles, and the lid provided with a diffusion test tube (Drägerwerk AG & Co. KGaA; Lübeck; Germany; Dräger Tube® Ammonia 20/a-D; Art. No. 8101301) was screwed on immediately. The evolution of ammonia was observed at 37° C. over 48 hours.

Measurement of Storage Stability

Approx. 10 g of the particular water-absorbing polymer particles are introduced into a snap-lid bottle (approx. 50 ml) and stored with no lid at 80° C. in a forced-air drying cabinet for 14 hours. The bottles are then closed immediately and cooled to ambient temperature.

The peroxide content is determined by method C-VI 6a part 2 (02) Peroxidzahl [peroxide number] in "Deutsche Einheitsmethoden zur Untersuchung von Fetten, Fettprodukten, Tensiden und verwandten Stoffen" [German standard methods for analyzing fats, fat products, surfactants and related substances], compiled and published by the Deutsche Gesellschaft für Fettwissenschaft e.V. [German Society for Fat Science], 2nd edition including 9th supplement, volume 2 (Wissenschaftliche Verlagsgesellschaft mbH, Stuttgart, 2004). 2.0 g of water-absorbing polymer particles are used each time, and a double determination is carried out in each case.

The results are reported relative to a closed sample stored at ambient temperature.

EXAMPLES

The examples were carried out with HySorb® B7055 or HySorb® B7065 (BASF SE; Ludwigshafen; Germany), commercial surface postcrosslinked water-absorbing polymer particles based on sodium acrylate with a degree of neutralization of 70 to 75 mol %.

Such surface postcrosslinked water-absorbing polymer particles are commercially available, for example, from BASF Aktiengesellschaft (trade name: HySorb®), from Stockhausen GmbH (trade name: Favor®) and from Nippon Shokubai Co., Ltd. (trade name: Aqualic®).

Example 1

20 g of water-absorbing polymer particles (HySorb® B7065; BASF SE; Germany) were weighed into a 50 ml glass bottle with 0.2 g of zinc peroxide (55% by weight; VWR International LLC; Buffalo Grove; US). Subsequently, the mixture was transferred into a large porcelain mortar (internal diameter 16 cm) and triturated there for approx. 5 minutes. In addition, the samples were homogenized once again in a tumbling mixer at 46 rpm for 20 minutes.

The resulting composition was analyzed. The results are compiled in table 1:

TABLE 1

Addition of zinc peroxide

| Example | CRC [g/g] | Time until attainment of 1500 ppm h of ammonia or value after 48 h |
|---|---|---|
| HySorb ® B7065 | 29.9 | 8.25 h |
| 1 | 29.5 | ammonia no longer detectable |

Example 2

Noninventive 300 g of water-absorbing polymer particles (HySorb® B7055; BASF SE; Germany) were introduced into a commercial food processor (Bosch Profi Mixx 47, model No. MUM4700/05, level 3, beaters). 6.12 g of a solution (163.3 g of 30% hydrogen peroxide made up to 1000 g with dist. water) were sprayed on with a spray atomizer (800 l/h of nitrogen). The mixture was stirred at level 1 for a further 10 minutes.

The resulting composition was analyzed. The results are compiled in table 2:

Example 3

Noninventive 300 g of water-absorbing polymer particles (HySorb® B7055; BASF SE; Germany) were introduced into a commercial food processor (Bosch Profi Mixx 47, model No. MUM4700/05, level 3, beaters). 6.12 g of a solution (156.59 g of hydrogen peroxide-urea adduct made up to 1000 g with dist. water) were sprayed on with a spray atomizer (800 l/h of nitrogen). The mixture was stirred at level 3 for a further 10 minutes.

The resulting composition was analyzed. The results are compiled in table 2:

Example 4

20 g of water-absorbing polymer particles (HySorb® B7055; BASF SE; Germany) were weighed into a 50 ml glass bottle with 0.383 g of zinc peroxide (71.6% by weight; Shan-Par Industries Pvt. Ltd.; India). Subsequently, this mixture was transferred into a porcelain mortar (internal diameter 8 cm) and triturated there. The triturated mixture was transferred into a 500 ml square plastic bottle, and a further 250 g of water-absorbing polymer particles (HySorb® B7055; BASF SE; Germany) were added. In addition, the sample was homogenized once again at 46 rpm in a tumbling mixer for 20 minutes. This mixture was introduced into a commercial food processor (Bosch Profi Mixx 47, model No. MUM4700/05, level 3, beaters), and sprayed with 5.96 g of a mixture of polyethylene glycol 400 and water (50:50 m/m) with a spray atomizer (800 l/h of nitrogen). The mixture was stirred at level 3 for a further 10 minutes.

The resulting composition was analyzed. The results are compiled in table 2:

Example 5

20 g of water-absorbing polymer particles (HySorb® B7055; BASF SE; Germany) were weighed into a 50 ml glass bottle with 1.044 g of magnesium peroxide (26% by weight; Sigma Aldrich). Subsequently, this mixture was transferred into a porcelain mortar (internal diameter 8 cm) and triturated there. The triturated mixture was transferred into a 500 ml square plastic bottle, and a further 250 g of water-absorbing polymer particles (HySorb® B7055; BASF SE; Germany) were added. In addition, the sample was homogenized once again at 46 rpm in a tumbling mixer for 20 minutes. This mixture was introduced into a commercial food processor (Bosch Profi Mixx 47, model No. MUM4700/05, level 3, beaters), and sprayed with 5.77 g of a mixture of polyethylene glycol 400 and water (50:50 m/m) with a spray atomizer (800 l/h of nitrogen). The mixture was stirred at level 3 for a further 10 minutes.

The resulting composition was analyzed. The results are compiled in table 2:

Example 6

20 g of water-absorbing polymer particles (HySorb® B7055; BASF SE; Germany) were weighed into a 50 ml glass bottle with 0.360 g of calcium peroxide (75% by weight; Sigma Aldrich). Subsequently, this mixture was transferred into a porcelain mortar (internal diameter 8 cm) and triturated there. The triturated mixture was transferred into u500 ml square plastic bottle, and a further 250 g of water-absorbing polymer particles (HySorb® B7055; BASF SE; Germany) were added. In addition, the sample was homogenized once again at 46 rpm in a tumbling mixer for 20 minutes. This mixture was introduced into a commercial food processor (Bosch Profi Mixx 47, model No. MUM4700/05, level 3, beaters), and sprayed with 5.79 g of a mixture of polyethylene glycol 400 and water (50:50 m/m) with a spray atomizer (800 l/h of nitrogen). The mixture was stirred at level 3 for a further 10 minutes.

The resulting composition was analyzed. The results are compiled in table 2:

Example 7

20 g of water-absorbing polymer particles (HySorb® B7055; BASF SE; Germany) were weighed into a 50 ml glass bottle with 0.300 g of lithium peroxide (90% by weight; Sigma Aldrich). Subsequently, this mixture was transferred into a porcelain mortar (internal diameter 8 cm) and triturated there. The triturated mixture was transferred into a 500 ml square plastic bottle, and a further 250 g of water-absorbing polymer particles (HySorb® B7055; BASF SE; Germany) were added. In addition, the sample was homogenized once again at 46 rpm in a tumbling mixer for 20 minutes. This mixture was introduced into a commercial food processor (Bosch Profi Mixx 47, model No. MUM4700/05, level 3, beaters), and sprayed with 5.62 g of a mixture of polyethylene glycol 400 and water (50:50 m/m) with a spray atomizer (800 l/h of nitrogen). The mixture was stirred at level 3 for a further 10 minutes.

The resulting composition was analyzed. The results are compiled in table 2:

TABLE 2

Measurement of storage stability

| Example | Metal peroxide | Peroxide content after storage |
|---------|----------------|-------------------------------|
| 2 | Hydrogen peroxide | 80% ± 5% |
| 3 | Hydrogen peroxide/urea | 77% ± 5% |
| 4 | Zinc peroxide | 104% ± 5% |
| 5 | Magnesium peroxide | 94% ± 5% |
| 6 | Calcium peroxide | 93% ± 5% |
| 7 | Lithium peroxide | 64% ± 5% |

The invention claimed is:

1. An odor-inhibiting composition comprising a mixture of water-absorbing polymer particles and at least one of zinc peroxide, magnesium peroxide, and calcium peroxide on the water-absorbing polymer particles,
wherein the composition comprises from 0.001 to 5% by weight of the at least one, of zinc peroxide, magnesium peroxide, and calcium peroxide, less than 10% by weight of water, and at least 90% by weight of the water-absorbing polymer particles.

2. The composition according to claim 1, wherein the water-absorbing polymer particles comprise at least 50% by weight of polymerized acrylic acid and/or salts thereof.

3. The composition according to claim 1, wherein the water-absorbing polymer particles have a centrifuge retention capacity of at least 15 g/g.

4. The composition according to claim 1 comprising from 0.1% to 1.5% by weight, of at least one of the zinc peroxide, magnesium peroxide, and calcium peroxide.

* * * * *